United States Patent
Proksa et al.

(10) Patent No.: US 9,761,024 B1
(45) Date of Patent: Sep. 12, 2017

(54) START IMAGE FOR SPECTRAL IMAGE ITERATIVE RECONSTRUCTION

(71) Applicant: KONINKLIJKE PHILIPS N.V., Eindhoven (NL)

(72) Inventors: Roland Proksa, Neu Wulmstorf (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/518,582

(22) PCT Filed: Oct. 12, 2015

(86) PCT No.: PCT/IB2015/057782
§ 371 (c)(1),
(2) Date: Apr. 12, 2017

(87) PCT Pub. No.: WO2016/063170
PCT Pub. Date: Apr. 28, 2016

Related U.S. Application Data

(60) Provisional application No. 62/065,893, filed on Oct. 20, 2014.

(51) Int. Cl.
*G06K 9/00* (2006.01)
*A61B 6/00* (2006.01)
*G06T 11/00* (2006.01)

(52) U.S. Cl.
CPC ....... *G06T 11/006* (2013.01); *G06T 2211/408* (2013.01); *G06T 2211/424* (2013.01)

(58) Field of Classification Search
CPC ............. G06T 11/006; G06T 2211/424; G06T 2211/408; G06T 7/0012; G06T 2207/10084; G06T 7/0081; A61B 6/032

(Continued)

(56) References Cited

U.S. PATENT DOCUMENTS 6,507,633 B1 * 1/2003 Elbakri ................. G06T 11/006
378/4
7,778,380 B2 * 8/2010 Altman ................. A61B 6/482
378/4

(Continued)

FOREIGN PATENT DOCUMENTS

| DE | 102008048682 | 12/2009 |
| WO | 2012104740 | 8/2012 |
| WO | 2015/011587 | 1/2015 |

OTHER PUBLICATIONS

Brown, et al., "Acceleration of ML iterative algorithms for CT by the use of fast start images", Proceedings of SPIE, vol. 8313, Feb. 23, 2012.

(Continued)

*Primary Examiner* — Sheela C Chawan

(57) ABSTRACT

A computing system (116) includes a reconstruction processor (114) configured to execute computer readable instructions, which cause the reconstruction processor to: receive, in electronic format, non-spectral projection data, reconstruct the non-spectral projection data to generate a non-spectral image, retrieve a non-spectral to spectral voxel value map for a basis material of interest from a set of non-spectral to spectral voxel value maps, generate a spectral iterative reconstruction start image based on the non-spectral image and the non-spectral to spectral voxel value map, and reconstruct a spectral image, in electronic format, for the material basis of interest from the non-spectral projection data with a spectral iterative reconstruction algorithm and the spectral iterative reconstruction start image.

20 Claims, 3 Drawing Sheets

(58) Field of Classification Search
USPC ....... 382/100, 128, 131, 162, 167, 254, 260, 382/264; 324/300, 318, 322, 307, 309; 378/1, 4, 5, 19
See application file for complete search history.

(56) References Cited

U.S. PATENT DOCUMENTS

| | | | | |
|---|---|---|---|---|
| 7,968,853 | B2* | 6/2011 | Altman | A61B 6/032 |
| | | | | 250/366 |
| 8,811,709 | B2* | 8/2014 | Wu | G06T 7/0012 |
| | | | | 378/4 |
| 9,269,168 | B2* | 2/2016 | Inglese | A61B 6/4241 |
| 2007/0147574 | A1* | 6/2007 | Bernard De Man | A61B 6/032 |
| | | | | 378/4 |
| 2015/0279005 | A1* | 10/2015 | Brendel | G06T 5/002 |
| | | | | 382/131 |
| 2016/0202364 | A1* | 7/2016 | Wang | A61B 6/032 |
| | | | | 378/5 |

OTHER PUBLICATIONS

Elbakri, et al., "Statistical Image Reconstruction for Polyenergetic X-Ray Computed Tomography", IEEE Transactions on Medical Imaging, vol. 21, No. 2, Feb. 2002.

Long et al., "Multi-Material Decomposition Using Statistical Image Reconstruction for Spectral CT," IEEE Transaction on Medical Imaging, vol. 33, No. 8, pp. 1614-1626, Aug. 2014.

\* cited by examiner

US 9,761,024 B1

START IMAGE FOR SPECTRAL IMAGE ITERATIVE RECONSTRUCTION

CROSS REFERENCE TO RELATED APPLICATIONS

This application is the U.S. National Phase application under 35 U.S.C. §371 of International Application No. PCT/IB2015/057782, filed Oct. 12, 2015, published as WO 2016/063170 on Apr. 28, 2016, which claims the benefit of U.S. Provisional Patent Application No. 62/065,893 filed Oct. 20, 2014. These applications are hereby incorporated by reference herein.

FIELD OF THE INVENTION

The following generally relates to spectral imaging and more particularly to generating a start image for a spectral image iterative reconstruction (IR), and is described with particular application to computed tomography (CT). However, the following is also amenable to other imaging applications.

BACKGROUND OF THE INVENTION

A computed tomography (CT) scanner includes an x-ray tube that emits x-ray radiation. The radiation traverses a subject or object located in a field of view and is attenuated thereby. A detector array detects the radiation traversing the field of view and produces a signal indicative thereof. A reconstructor reconstructs the signal to produce one or more images. Reconstruction algorithms have included non-iterative reconstruction algorithms (e.g., filtered back projection) and iterative reconstruction algorithms (e.g., statistical, numerical, etc.). Iterative reconstruction algorithms start with an initial image and then iteratively update the initial image, through a series of intermediate images, until stopping criteria is satisfied. Unfortunately, this process has been time intensive, especially when the initial image is far away from the final image (e.g., an initial image of all zeros).

SUMMARY OF THE INVENTION

In one aspect, a computing system includes a reconstruction processor that is configured to execute computer readable instructions, which cause the reconstruction processor to: receive, in electronic format, non-spectral projection data, reconstruct the non-spectral projection data to generate a non-spectral image. The reconstruction processor further retrieves a non-spectral to spectral voxel value map for a basis material of interest from a set of non-spectral to spectral voxel value maps. The reconstruction processor further generates a spectral iterative reconstruction start image based on the non-spectral image and the non-spectral to spectral voxel value map. The reconstruction processor further reconstructs a spectral image, in electronic format, for the material basis of interest from the non-spectral projection data with a spectral iterative reconstruction algorithm and the spectral iterative reconstruction start image.

In another aspect, a method comprises receiving, in electronic format, non-spectral projection data from a scan. The method further includes reconstructing the non-spectral projection data to generate a non-spectral image. The method further includes retrieving a non-spectral to spectral voxel value map for a basis material of interest from a set of non-spectral to spectral voxel value maps. The method further includes generating a spectral iterative reconstruction start image based on the non-spectral image and the non-spectral to spectral voxel value map. The method further includes reconstructing a spectral image, in electronic format, for the material basis of interest from the non-spectral projection data with a spectral iterative reconstruction algorithm and the spectral iterative reconstruction start image.

In yet another aspect, an imaging system includes a detector array that receives radiation traversing an examination region and generates non-spectral projection data indicative of the examination region and a computing system. The computing system includes a reconstruction processor configured to execute computer readable instructions, which cause the reconstruction processor to receive, in electronic format, non-spectral projection data. The computer readable instructions further cause the reconstruction processor to reconstruct the non-spectral projection data to generate a non-spectral image. The computer readable instructions further cause the reconstruction processor to retrieve a non-spectral to spectral voxel value map for a basis material of interest from a set of non-spectral to spectral voxel value maps. The computer readable instructions further cause the reconstruction processor to generate a spectral iterative reconstruction start image based on the non-spectral image and the non-spectral to spectral voxel value map. The computer readable instructions further cause the reconstruction processor to reconstruct a spectral image, in electronic format, for the material basis of interest from the non-spectral projection data with a spectral iterative reconstruction algorithm and the spectral iterative reconstruction start image.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
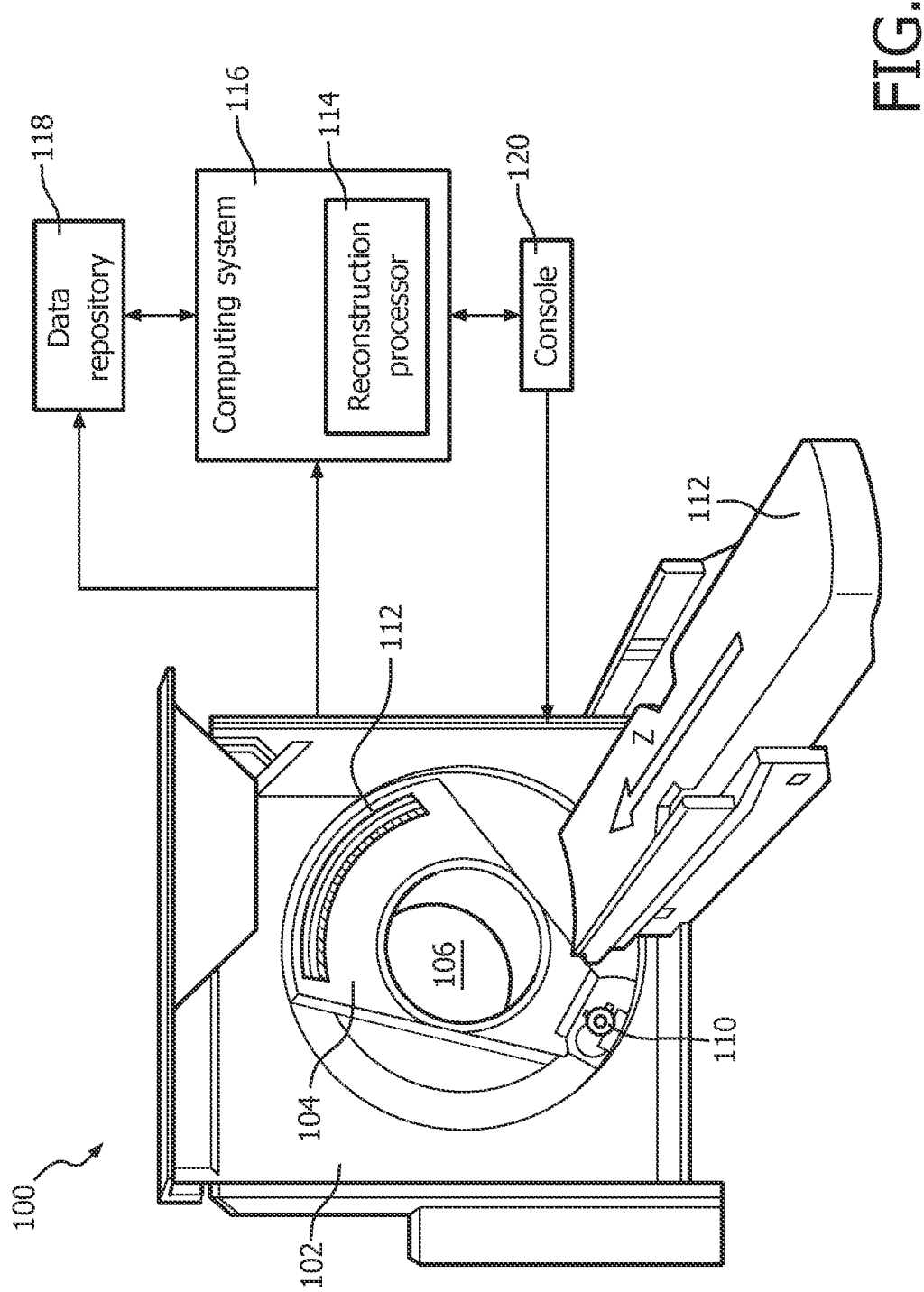
FIG. 1 schematically illustrates an example imaging system with a reconstruction processor that generates a spectral IR start image from a non-spectral image and a mapping between non-spectral and spectral values.

FIG. 1 illustrates an example imaging system 100 such as a computed tomography (CT) system. The imaging system 100 includes a stationary gantry 102 and a rotating gantry 104, which is rotatably supported by the stationary gantry 102. The rotating gantry 104 rotates around an examination region 106 about a longitudinal or z-axis "Z". The imaging system 100 further includes a radiation source 110, such as an x-ray tube, that is rotatably supported by the rotating gantry 104, rotates with the rotating gantry 104, and emits x-ray radiation that traverses the examination region 106.

The imaging system 100 further includes a detector array 112 that subtends an angular arc opposite the examination region 106, relative to the radiation source 110. The detector array 112 detects radiation that traverses the examination region 106 and generates non-spectral projection data indicative thereof. In one embodiment, the detector array 112 includes a multi-layer detector array with at least an upper layer and a lower layer. In this instance, the non-spectral projection data includes data from the upper layer, the lower layer, a combination of the data from the upper and lower layers, etc. An example of multi-layer detector includes a double decker detector such as the double decker detector described in U.S. Pat. No. 7,968,853 B2, filed Apr. 10, 2006, and entitled "Double Decker Detector for Spectral CT," the entirety of which is incorporated herein by reference. In another embodiment, the detector array 112 includes direct conversion photon counting detector pixels. With such pixels, a generated signal will include an electrical current or voltage having a peak amplitude or a peak height that is indicative of the energy of a detected photon. The direct conversion photon counting detector pixels may include any suitable direct conversion material such as CdTe, CdZnTe, Si, Ge, GaAs, or other direct conversion material.

The imaging system 100 further includes a reconstruction processor 114 that receives, in electronic format, the non-spectral projection data from the detector array 112 and/or other device (e.g., other imaging system, a storage device, etc.). The reconstruction processor 114 also receives scan parameters (e.g., tube voltage, filtration, etc.) and/or characteristics of a scanned object or subject (e.g., size, region of interest, etc.). Such information can be obtained from a field in the electronic file, the imaging protocol, user input, etc. The reconstruction processor 114 processes the non-spectral projection data and reconstructs spectral images such as one or more of a photoelectric image, a Compton scatter image, an iodine image, a virtual non contrast image, a bone image, a soft tissue image, and/or other basis material image. As utilized herein, the term "image" includes two-dimensional images and three-dimensional volumetric image data.

As described in greater detail below, in one non-limiting instance, the reconstruction processor 114, for a particular basis material, derives a spectral IR start image from a non-spectral image generated with the non-spectral projection data, and begins the spectral image IR with the spectral IR start image. For two or more basis materials, the reconstruction processor 114 derives a spectral IR start image for each basis material. Beginning the spectral image IR with the spectral IR start image allows for reducing reconstruction time relative to a configuration in which another start image (e.g., all zeroes) is utilized since the spectral IR start image will be closer to the final spectral image. That is, the spectral IR start image will already contain edge and high frequency components, which typically require many iterations, and the low frequency components, which require less iterations, will be updated through the iterative process.

The illustrated reconstruction processor 114 is part of a computing system 116 and is implemented via one or more processors (e.g., a central processing unit (CPU), a microprocessor, etc.). The processor(s) executes one or more computer executable instructions embedded or encoded on computer readable storage medium of the computing system 116, which excludes transitory medium and includes physical memory and/or other non-transitory medium. A computer executable instruction can also be carried by transitory medium such as a carrier wave, signal, and/or other transitory medium.

The imaging system 100 further includes a data repository 118, which stores projection data and/or reconstructed images of the imaging system 100 and/or other imaging system. The illustrated data repository 118 is part of the imaging system 100, such as physical memory of the imaging system 100. In another embodiment, the data repository 118 is separate from the imaging system 100, e.g., part of a picture archiving and communication system (PACS), a radiology information system (RIS), a hospital information system (HIS), an electronic medical record (EMR), a database, a server, and/or other data repository.

The imaging system 100 further includes a computer that serves as an operator console 120 with a human readable output device such as a monitor and an input device such as a keyboard, mouse, etc. Software resident on the console 120 allows the operator to interact with and/or operate the scanner 100 via a graphical user interface (GUI) or otherwise. For example, the console 120 allows the operator to select a scan protocol, a spectral image IR algorithm and/or non-spectral image reconstruction algorithm, initiate scanning, etc.

The imaging system 100 further includes a subject support 122, such as a couch, that supports a human or animal subject or an object in the examination region 106. The subject support 122 is movable in coordination with scanning so as to guide the human or animal subject or object with respect to the examination region 106 before, during and/or after scanning, and for loading and/or unloading the subject or the object.

Figure 2:
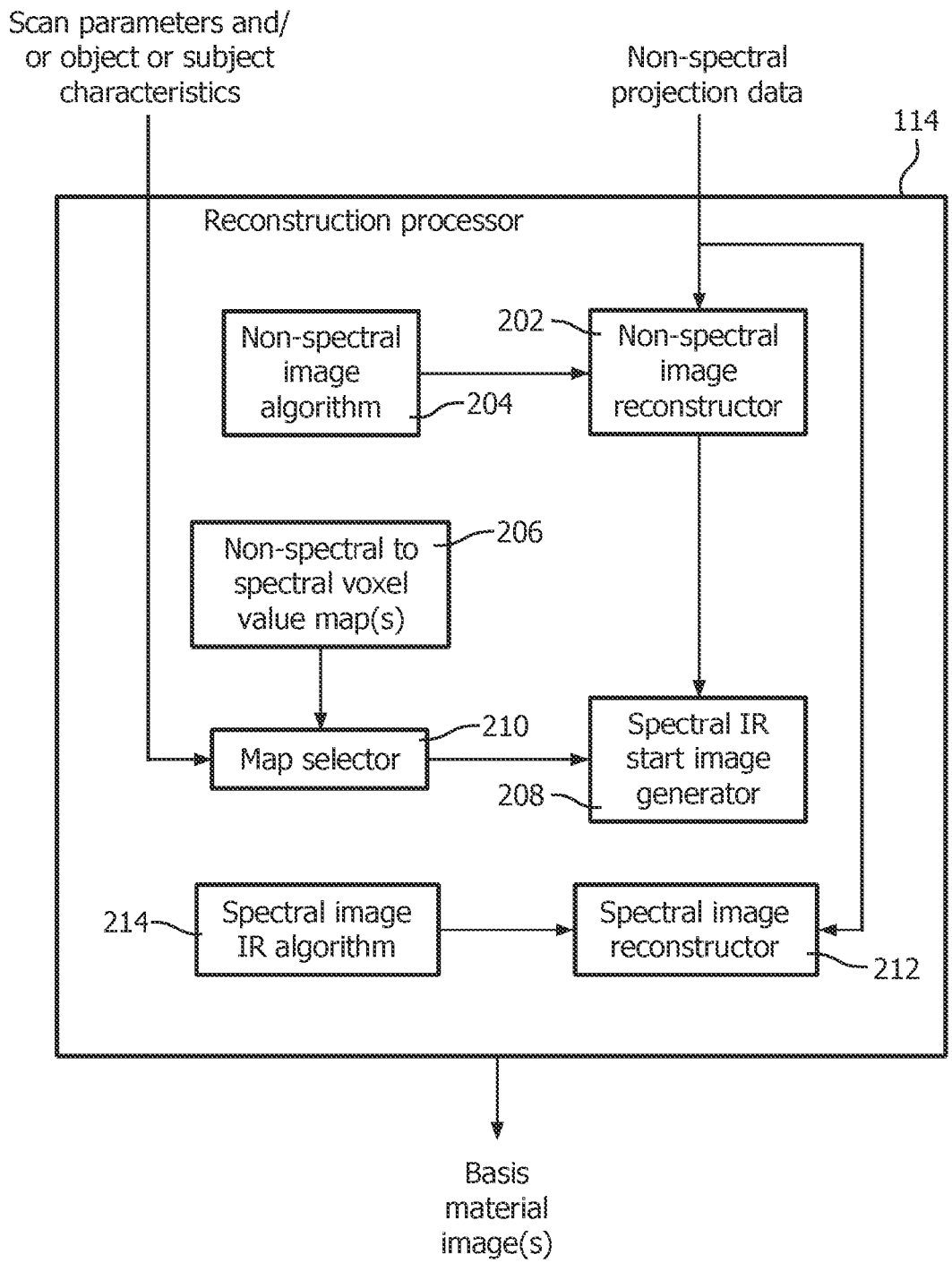
FIG. 2 schematically illustrates an example of the reconstruction processor.

FIG. 2 schematically illustrates an example of the reconstruction processor 114. The reconstruction processor 114 receives, as input, non-spectral projection data. From above, such information can be obtained from the data repository 118 and/or an imaging system (e.g., the imaging system 100 and/or other imaging system). The reconstruction processor 114 further receives, as input, scan parameters (e.g., tube voltage, filtration, etc.) and/or characteristics of a scanned object or subject (e.g., size, region of interest, etc.). From above, such information can be obtained from the electronic file, the imaging protocol, user input, etc.

The reconstruction processor 114 includes a non-spectral image reconstructor 202, which reconstructs the received non-spectral projection data with a non-spectral image reconstruction algorithm 204 and generates a non-spectral image(s). The reconstruction processor 114 further includes one or more non-spectral to spectral voxel value maps 206, each including a mapping between voxels of a non-spectral image and voxels of a spectral image. In one instance, the one or more non-spectral to spectral voxel value maps 206 are included in one or more look-up tables (LUTs). For example, the voxel values of the non-spectral image and voxel values of the spectral image may be grouped in pairs or otherwise. In another instance, the one or more non-spectral to spectral voxel value maps 206 is stored in one or more polynomials and/or otherwise.

A map of the maps 206 can be generated for a basis material by taking a training set of non-spectral images and a training set of basis material images for an acquisition with similar scan parameters (e.g., tube voltage, filtration, etc.) and for a similar size and/or region of an object or subject, and calculating a mean material basis image for the basis material (e.g., Compton scatter, photo-electric, iodine, virtual non-contrast, bone, soft tissue, etc.) value for each non-spectral image voxel value. For example, for all voxels (or a sub-set thereof) with a value of V±T (where V, e.g., is in Hounsfield units and T is a tolerance and takes into account noise) in the set of training non-spectral images, values of the same voxels (i.e., the same x,y,z coordinates) in the set of training basis material image are averaged, and the map for that basis material is populated with the value V±T and the corresponding mean basis material voxel value.

The training set of non-spectral images and the training set of basis material images with the similar scan parameters can be for the same object or subject and/or a different but similar object or subject (e.g., similar in size, geometry, etc.). This includes the same object or subject corresponding to the input non-spectral projection data and/or a different but similar object or subject. The training set of non-spectral images and/or the training set of basis material images can be generated using an iterative reconstruction and/or a non-iterative reconstruction. The one or more non-spectral to spectral voxel value maps 206 can be generated during assembly, testing and calibration at the factory and/or at an end user facility. The one or more non-spectral to spectral voxel value maps 206 can be stored in local memory of the imaging system 100 and/or memory remote from the imaging system 100 but accessible to the imaging system 100 via a network and/or otherwise.

The reconstruction processor 114 further includes a spectral IR start image generator 208 that generates a spectral IR start image based on a map from one or more non-spectral to spectral voxel value maps 206 and the reconstructed non-spectral image. For the map, a map selector 210 retrieves a map 206 from the one or more non-spectral to spectral voxel value maps 206 based on the input scan parameters and/or object or subject characteristics. Where the individual maps 206 are combined into a single map 206, the single map 206 is selected. The spectral IR start image generator 208 then retrieves the spectral values in the selected map 206 that corresponds to the non-spectral values in the non-spectral image. Where the selected map 206 does not include an exact match for a non-spectral value, the spectral IR start image generator 208 selects a closest value, interpolates between neighboring values, etc.

The reconstruction processor 114 further includes a spectral image reconstructor 212, which reconstructs, iteratively, spectral images from the non-spectral projection data with a spectral image IR algorithm 214, using the spectral IR start image as the initial image. The reconstruction processor 114 can generate one or more spectral images for one or more basis materials using one or more basis material specific IR start images to iteratively reconstruct the one or more spectral images. Again, examples of basis material include, but are not limited to, a photoelectric image, a Compton scatter image, an iodine image, a virtual non-contrast image, a bone image, a soft tissue image, and/or other basis material image.

With the approach described herein, the initial IR image (i.e., the spectral IR start image) contains edge and high frequency components of the non-spectral image. As such, the initial spectral image is closer to the final spectral image. Generally, the edge and high frequency components require many iterations, and low frequency components require less iterations. As a result, the approach described herein will require less iterations and hence reconstruction time relative to a configuration in which a different start image (e.g., all zeroes) is used.

Figure 3:
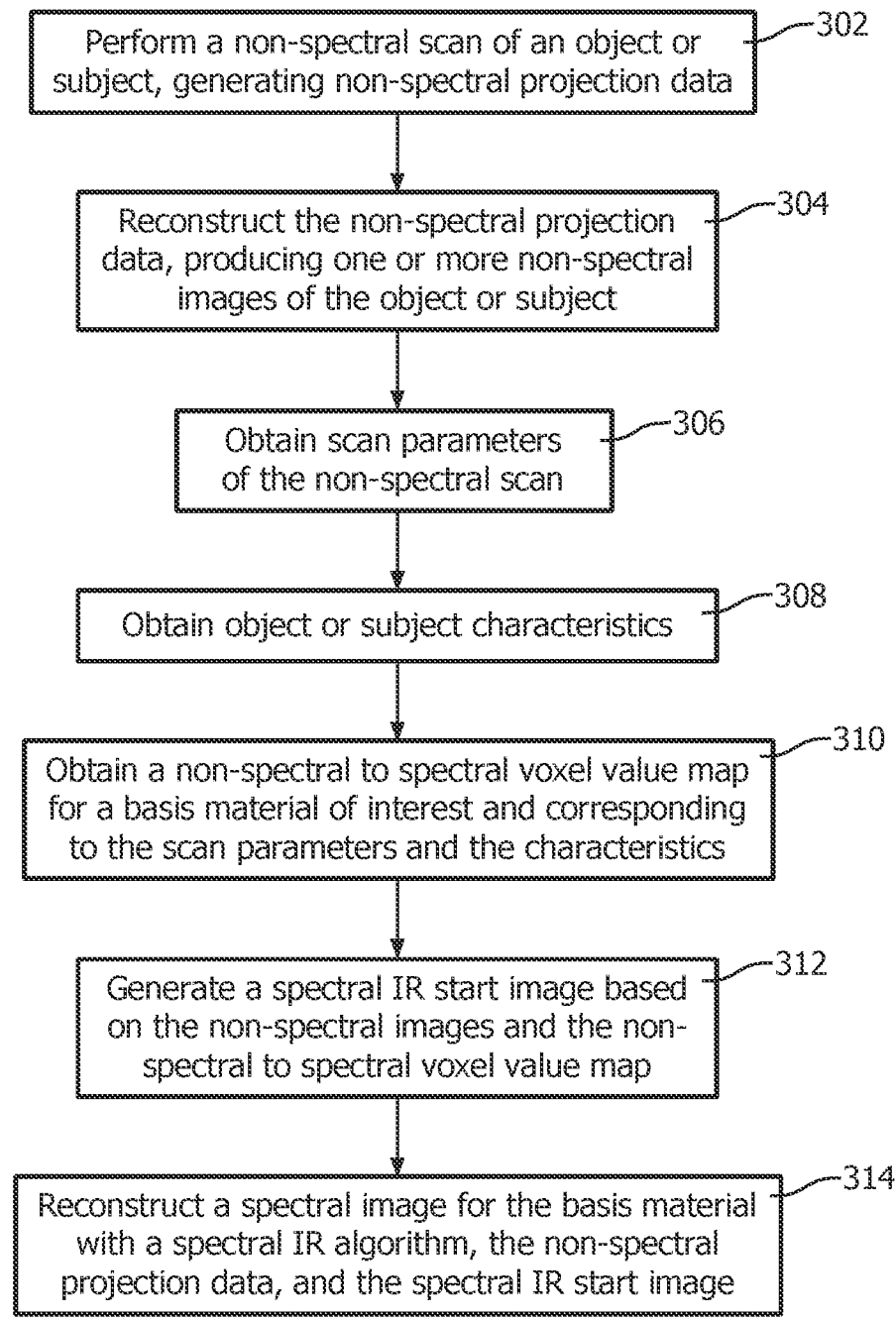
FIG. 3 illustrates a method for generating a spectral IR start image from a non-spectral image and a mapping between non-spectral and spectral values for a spectral image IR.

FIG. 3 illustrates a method in accordance with an embodiment described herein.

It is to be appreciated that the ordering of the below acts is for explanatory purposes and not limiting. As such, other orderings are also contemplated herein. In addition, one or more of the acts may be omitted and/or one or more other acts may be included.

At 302, a non-spectral scan of an object or subject is performed, producing non-spectral projection data of the object or subject.

At 304, the non-spectral projection data is reconstructed, producing one or more non-spectral images.

At 306, scan parameters of the non-spectral scan are obtained. As described herein, such parameters include the x-ray tube voltage, the filtration, and/or other parameters, which can be obtained from the data file, the imaging protocol, and/or otherwise.

At 308, characteristics of the scanned object or subject are obtained. As described herein, such information can be obtained from the data file, the imaging protocol, and/or otherwise. In a variation, this act is omitted.

At 310, a non-spectral to spectral voxel value map for a basis material of interest and corresponding to the scan parameters and object or subject characteristics is obtained. Where there is more than one basis material of interest, a non-spectral to spectral voxel value map is obtained for each basis material.

At 312, a spectral IR start image is generated for the basis material based on the non-spectral image and the non-spectral to spectral voxel value map, as described herein and/or otherwise.

At 314, a spectral image for the basis material is reconstructed with a spectral IR algorithm, the non-spectral projection data, and the spectral IR start image. An example of a spectral IR algorithm is described in application serial number PCT/IB2014/062846, filed Jul. 4, 2014, and entitled "HYBRID (SPECTRAL/NON-SPECTRAL) IMAGING DETECTOR ARRAY AND CORRESPONDING PROCESSING ELECTRONICS," the entirety of which is incorporated herein by reference, and in Long et al., "Multi-Material Decomposition Using Statistical Image Reconstruction for Spectral CT," IEEE Transaction on Medical Imaging, Vol. 33, No. 8, pp. 1614-1626, August 2014.

At least a portion of the method discussed herein may be implemented by way of computer readable instructions, encoded or embedded on computer readable storage medium (which excludes transitory medium), which, when executed by a computer processor(s), causes the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A computing system, comprising:
   a reconstruction processor configured to execute computer readable instructions, which cause the reconstruction processor to:
   receive, in electronic format, non-spectral projection data;
   reconstruct the non-spectral projection data to generate a non-spectral image;
   retrieve a non-spectral to spectral voxel value map for a basis material of interest from a set of non-spectral to spectral voxel value maps;
   generate a spectral iterative reconstruction start image based on the non-spectral image and the non-spectral to spectral voxel value map; and
   reconstruct a spectral image, in electronic format, for the material basis of interest from the non-spectral projection data with a spectral iterative reconstruction algorithm and the spectral iterative reconstruction start image.

2. The computing system of claim 1, wherein the non-spectral to spectral voxel value map provides a mapping between a voxel value of the non-spectral image to a voxel value for the basis material.

3. The computing system of claim 2, wherein the reconstruction processor identifies a voxel value of a voxel of the non-spectral image in the non-spectral to spectral voxel value map, retrieves the corresponding voxel value for the basis material, and populates a same voxel coordinate in the spectral iterative reconstruction start image with the retrieved voxel value.

4. The computing system of claim 1, where the reconstruction processor:
receives an input indicative of at least one scan parameter of the non-spectral scan;
identifies the non-spectral to spectral voxel value map for the basis material from the set of non-spectral to spectral voxel value maps for the basis material based on the at least one scan parameter, wherein the set of non-spectral to spectral voxel value maps includes a plurality of different non-spectral to spectral voxel value maps, each for a different combination of the at least one scan parameter; and
retrieves the identified non-spectral to spectral voxel value map; and
generates the spectral iterative reconstruction start image with the retrieved the identified non-spectral to spectral voxel value map.

5. The computing system of claim 4, wherein the at least one scan parameter includes a at least one of an x-ray tube voltage or a beam filtration of the non-spectral scan that generated the non-spectral projection data.

6. The computing system of claim 4, wherein the non-spectral image includes voxels having values indicative of an object or subject, and the reconstruction processor:
receives an input indicative of at least one of an x-ray tube voltage or a beam filtration of the at least one scan parameter and a characteristic of the object or the subject;
identifies the non-spectral to spectral voxel value map for the basis material from the set of non-spectral to spectral voxel value maps for the basis material based on the at least one scan parameter and the characteristic, wherein the set of non-spectral to spectral voxel value maps includes a plurality of different non-spectral to spectral voxel value maps, each for a different combination of the at least one scan parameter and the characteristic; and
retrieves the identified non-spectral to spectral voxel value map; and
generates the spectral iterative reconstruction start image with the retrieved the identified non-spectral to spectral voxel value map.

7. The computing system of claim 6, wherein the characteristic includes at least one of a size or a region of interest of the object or subject.

8. The computing system of claim 1, wherein the reconstruction processor:
receives the set of non-spectral to spectral voxel value maps; and
stores the set of non-spectral to spectral voxel value maps, wherein each voxel value pair of a non-spectral voxel value and a spectral voxel value includes a voxel value of a preselected training set of non-spectral images and a corresponding value of a preselected training set of spectral images for the basis material.

9. The computing system of claim 1, wherein the set of non-spectral to spectral voxel value map is included in at least one of a look-up table or a polynomial.

10. The computing system of claim 1, wherein the basis material of interest includes at least one of a photo-electric basis material, a Compton scatter basis material, an iodine basis material, a virtual non contrast basis material, bone, or soft tissue.

11. A method, comprising:
receiving, in electronic format, non-spectral projection data from a scan;
reconstructing the non-spectral projection data to generate a non-spectral image;
retrieving a non-spectral to spectral voxel value map for a basis material of interest from a set of non-spectral to spectral voxel value maps;
generating a spectral iterative reconstruction start image based on the non-spectral image and the non-spectral to spectral voxel value map; and
reconstructing a spectral image, in electronic format, for the material basis of interest from the non-spectral projection data with a spectral iterative reconstruction algorithm and the spectral iterative reconstruction start image.

12. The method of claim 11, wherein the non-spectral to spectral voxel value map provides a mapping between a voxel value of the non-spectral image to a voxel value for the basis material.

13. The method of claim 12, wherein the reconstruction processor identifies a voxel value of a voxel of the non-spectral image in the non-spectral to spectral voxel value map, retrieves the corresponding voxel value for the basis material, and populates a same voxel coordinate in the spectral iterative reconstruction start image with the retrieved voxel value.

14. The method of claim 11, further comprising:
receiving an input indicative of at least one of an x-ray tube voltage or a beam filtration of the non-spectral scan that generated the non-spectral projection data;
identifying the non-spectral to spectral voxel value map for the basis material from the set of non-spectral to spectral voxel value maps for the basis material based on the at least one of x-ray tube voltage or the beam filtration, wherein the set of non-spectral to spectral voxel value maps includes a plurality of different non-spectral to spectral voxel value maps, each for a different combination of the at least one of x-ray tube voltage or the beam filtration; and
retrieving the identified non-spectral to spectral voxel value map; and
generating the spectral iterative reconstruction start image with the retrieved identified non-spectral to spectral voxel value map.

15. The method of claim 11, wherein the non-spectral image includes voxels having values indicative of an object or subject, and further comprising:
receiving an input indicative of at least one of an x-ray tube voltage or a beam filtration of the non-spectral scan that generated the non-spectral projection data and a characteristic of the object or the subject;
identifying the non-spectral to spectral voxel value map for the basis material from the set of non-spectral to spectral voxel value maps for the basis material based on the at least one of x-ray tube voltage or the beam filtration and the characteristic, wherein the set of non-spectral to spectral voxel value maps includes a plurality of different non-spectral to spectral voxel value maps, each for a different combination of the at least one of x-ray tube voltage or the beam filtration and the characteristic; and retrieving the identified non-spectral to spectral voxel value map; and generating the spectral iterative reconstruction start image with the retrieved identified non-spectral to spectral voxel value map.

16. The method of claim 11, wherein the further comprising:

receive the set of non-spectral to spectral voxel value maps; and store the set of non-spectral to spectral voxel value maps, wherein each voxel value pair of a non-spectral voxel value and a spectral voxel value includes a voxel value of a preselected training set of non-spectral images and a corresponding value of a preselected training set of spectral images for the basis material.

17. The method of claim 11, wherein the set of non-spectral to spectral voxel value map is included in at least one of a look-up table or a polynomial.

18. The method of claim 11, wherein the basis material of interest includes at least one of a photo-electric basis material, a Compton scatter basis material, an iodine basis material, a virtual non contrast basis material, bone, or soft tissue.

19. An imaging system, comprising:

a detector array the receives radiation traversing an examination region and generates non-spectral projection data indicative of the examination region; and a computing system, comprising:

a reconstruction processor configured to execute computer readable instructions, which cause the reconstruction processor to:

receive, in electronic format, non-spectral projection data;

reconstruct the non-spectral projection data to generate a non-spectral image;

retrieve a non-spectral to spectral voxel value map for a basis material of interest from a set of non-spectral to spectral voxel value maps;

generate a spectral iterative reconstruction start image based on the non-spectral image and the non-spectral to spectral voxel value map; and reconstruct a spectral image, in electronic format, for the material basis of interest from the non-spectral projection data with a spectral iterative reconstruction algorithm and the spectral iterative reconstruction start image.

20. The imaging system of claim 19, wherein the reconstruction processor identifies a voxel value of a voxel of the non-spectral image in the non-spectral to spectral voxel value map, retrieves the corresponding voxel value for the basis material, and populates a same voxel coordinate in the spectral iterative reconstruction start image with the retrieved voxel value.

* * * * *